(12) United States Patent
Ganz

(10) Patent No.: US 6,764,501 B2
(45) Date of Patent: Jul. 20, 2004

(54) APPARATUS AND METHOD FOR TREATING ATHEROSCLEROTIC VASCULAR DISEASE THROUGH LIGHT STERILIZATION

(76) Inventor: Robert A. Ganz, 13956 Emerald Ridge, Minnetonka, MN (US) 55305

( * ) Notice: Subject to any disclaimer, the term of this patent is extended or adjusted under 35 U.S.C. 154(b) by 0 days.

(21) Appl. No.: 10/119,855

(22) Filed: Apr. 9, 2002

(65) Prior Publication Data

US 2002/0147443 A1 Oct. 10, 2002

Related U.S. Application Data

(60) Provisional application No. 60/282,780, filed on Apr. 10, 2001.

(51) Int. Cl.$^7$ .................................................. A61N 5/00
(52) U.S. Cl. ............................ 607/92; 607/94; 607/88; 606/3
(58) Field of Search .................... 607/88–94; 600/9–12, 600/2, 3, 7

(56) References Cited

U.S. PATENT DOCUMENTS

| | | | |
|---|---|---|---|
| 4,773,899 A | * | 9/1988 | Spears .......................... 604/20 |
| 4,848,336 A | | 7/1989 | Fox et al. |
| 4,998,930 A | | 3/1991 | Lundahl |
| 5,041,108 A | | 8/1991 | Fox et al. |
| 5,059,191 A | | 10/1991 | Beyer et al. |
| 5,188,632 A | * | 2/1993 | Goldenberg ..................... 606/7 |
| 5,334,171 A | | 8/1994 | Kaldany |
| 5,405,369 A | | 4/1995 | Selman et al. |
| 5,531,662 A | | 7/1996 | Carr |
| 5,591,199 A | | 1/1997 | Porter et al. |
| 5,637,877 A | * | 6/1997 | Sinofsky ................... 250/492.1 |
| 5,647,840 A | | 7/1997 | D'Amelio et al. |
| 5,653,683 A | | 8/1997 | D'Andrea |
| 5,741,246 A | * | 4/1998 | Prescott ......................... 606/7 |
| 5,769,844 A | * | 6/1998 | Ghaffari ....................... 606/16 |
| 5,843,143 A | * | 12/1998 | Whitehurst ................... 607/88 |
| 5,845,640 A | * | 12/1998 | Lawandy ..................... 600/473 |
| 5,855,595 A | * | 1/1999 | Fujishima et al. ............. 607/90 |
| 5,871,522 A | * | 2/1999 | Sentilles ....................... 607/94 |
| 5,989,283 A | * | 11/1999 | Wilkens ....................... 607/88 |
| 6,061,591 A | | 5/2000 | Freitag et al. |
| 6,070,096 A | | 5/2000 | Hayashi | |

FOREIGN PATENT DOCUMENTS

JP          10-94583          4/1998

OTHER PUBLICATIONS

U.S. patent application Ser. No. 09/338,687, Ganz.
U.S. patent application Ser. No. 09/598,653, Ganz.
U.S. patent application Ser. No. 10/119,976, Ganz et al.
C.E. Millson et al., Ex–Vivo Treatment of Gastric Helicobacter Infection by Photodynamic Therapy; Journal of Photo–chemistry and Photobiology B: Biology 32 (1996) 59–65 London.

(List continued on next page.)

*Primary Examiner*—Michael Peffley
(74) *Attorney, Agent, or Firm*—James V. Harmon

(57) ABSTRACT

Atherosclerotic vascular disease is treated by exposing the interior of an artery or vein to visible or ultraviolet light of a selected spectrum to thereby sterilize the artery, eradicating infectious pathogens and reverse the pathogenesis of atherosclerotic artery disease. A fiber optic bundle positioned via an intra-arterial catheter is connected to an appropriate light radiation source located outside of the body during treatment. In another form, the light energy is produced by means of a light energy source located at the distal tip of the instrument shaft positioned centrally within the atherosclerotic plaque formation. In this case, the power source at the distal tip of the instrument can be a light emitting diode (LED) or a transparent tube containing a chemilumlumenescent substance for producing cool light energy within the vessel to destroy the pathogenic microorganisms in the surrounding plaque or vessel without damage to the body tissue of the patient.

17 Claims, 3 Drawing Sheets

OTHER PUBLICATIONS

C.E. Millson et al., The Killing of Helicobacter pylori by Low Power Laser Light in the Presence of a Photosensitizer; J Med Microbiology vol. 44 (1996) 245–252.

Martinetto P., et al. Bactercidal Effects Induced by Laser Irradiation and Haematoporphyrin Against Gram–positive and Gram–negative Microorganisms. Drugs Exp. Clin Res. XII (4): 335–342, 1986.

Kubey W., et al. In Vitro Studies on the Microbicidal Effectiveness of a Xenon–based Ultraviolet Light Device for Continuous Ambulatory Peritoneal Connections. Blood Purif. 9 (2): 102–108, 1991.

* cited by examiner

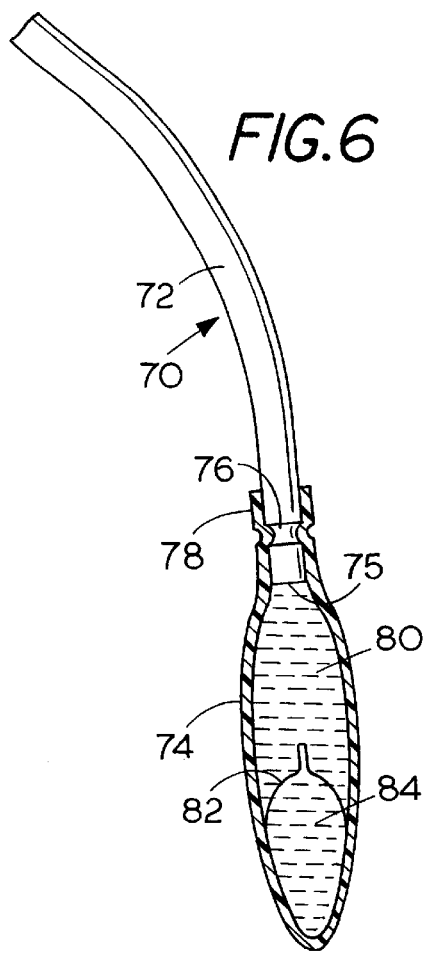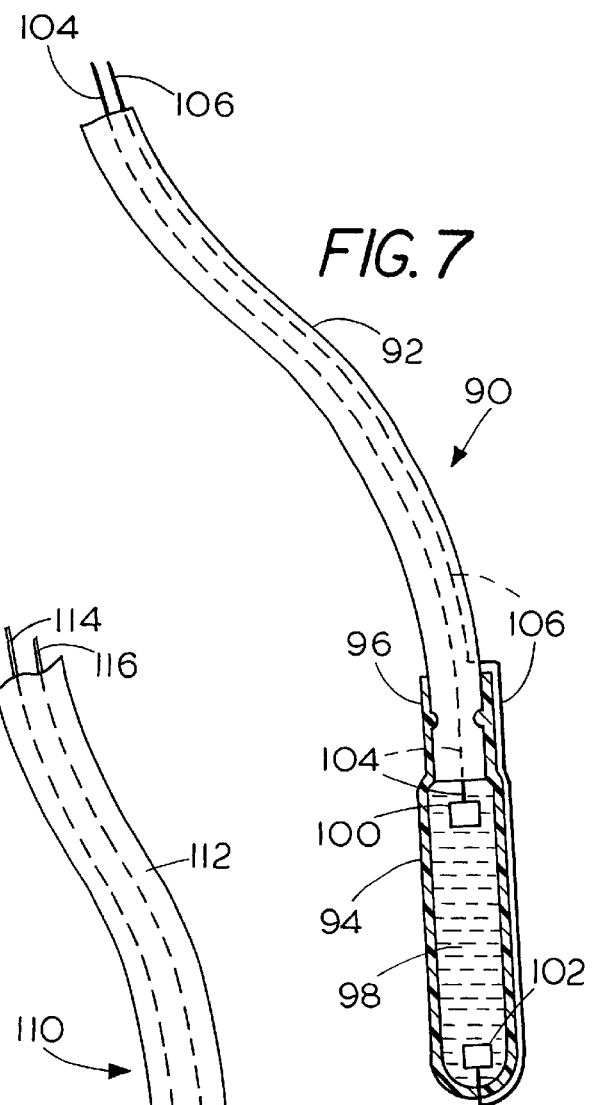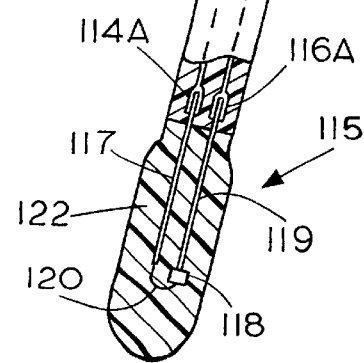

US 6,764,501 B2

APPARATUS AND METHOD FOR TREATING ATHEROSCLEROTIC VASCULAR DISEASE THROUGH LIGHT STERILIZATION

This application claims benefit of Provisional application No. 60/282,780 filed Apr. 10, 2001.

FIELD OF THE INVENTION

This invention relates to an apparatus and method for treating atherosclerotic vascular disease by means of light radiation.

BACKGROUND OF THE INVENTION

Atherosclerotic vascular disease represents one of the major health problems in the world. It is the number one cause of death in the United States, being responsible for one third of all reported mortality on an annual basis. The magnitude of the problem is staggering; in the United States alone over 60 million people have some form of atherosclerotic vascular disease. In 1995, approximately 1,000,000 people died from this problem. Atherosclerotic vascular disease ranks as the leading reason for social security disability, limitation in physical activity, and hospital bed use accounting for 46 million bed days in 1994. The direct and indirect costs of treating this scourge is in the hundreds of billions of dollars on an annual basis.

Although research in this area has been intense, the exact cause of atherosclerotic artery disease remains unknown. Atherosclerosis is the descriptive term for thickened and hardened lesions of the arteries. It results from fatty deposits that build up in the innermost lining, or intima, of the artery. The lesions are generally eccentric and if they become sufficiently large, can occlude the artery and thus the blood supply to a tissue or organ, resulting in ischemia or necrosis. If this occurs, it often leads to the characteristic clinical outcomes of myocardial infarction (heart attack), cerebral infarction (stroke), gangrene of the extremities, etc.

The exact cause of the fatty build-up is not known although the stages of progression are well described, and certain risk factors well-identified, such as smoking, high cholesterol levels, obesity, diabetes etc. More recently, evidence has pointed to a potential infectious cause of atherosclerotic vascular disease. Cytomegalo virus, Chlamydia and Helicobacter pylori have all been associated with atherosclerotic disease. The infectious pathogens are presumed to cause chronic inflammation, which results in atherosclerotic deposition.

In one study involving Helicobacter pylori, 38 atherosclerotic plaques were obtained at carotid endocardectomy, and examined for the presence or absence of bacteria. The researchers used morphological and immunohistochemical techniques to do this, and a highly sensitive polymerase chain reaction method to search for Helicobacter DNA. As a control, the researchers examined 7 carotid arteries obtained at autopsy from subjects without carotid atherosclerosis. The researchers detected the presence of Helicobacter pylori DNA in 20 out of 38 atheromatous plaques, and morphological/immunohistochemical evidence of bacteria in 10 of the DNA-positive plaques. None of the 7 normal carotid arteries were positive for Helicobacter pylori (Ameriso, 2001).

If atherosclerotic artery disease were to be infectious in etiology, antibiotics probably would not work well due to lack of penetration into dense plaque.

In view of these and other deficiencies of the prior art it is the primary object of the present invention to provide an apparatus and method for treating atherosclerotic vascular disease using light radiation.

Another more specific object is to treat vascular disease of the character described using light radiation without significant damage to the vessel or surrounding body tissue.

A further object of the present invention is to provide an apparatus of the type described which is characterized by emitting radiation which is destructive to pathogenic microorganisms that cause and/or contribute to atherosclerotic disease without producing sufficient heat to damage body tissues.

Yet another object of the invention is to provide an apparatus of the character described which is small enough for insertion into relatively small blood vessels such as the coronary arteries but is also useful for treating blood vessels throughout the body including cerebral vessels and peripheral vessels that are partially or completely occluded by atherosclerotic plaque.

These and other more detailed and specific objects of the present invention will be better understood by reference to the following figures and detailed description which illustrate by way of example of but a few of the various forms of the invention within the scope of the appended claims.

BRIEF DESCRIPTION OF THE DRAWINGS

FIG. 6 is a partial longitudinal sectional view of another light energy distribution head on a greatly enlarged scale.

FIG. 7 is a partial longitudinal sectional view of another form of energy distribution head on a greatly enlarged scale and FIG. 8 is a greatly enlarged partial longitudinal sectional view of another form of light energy distribution head in accordance with the invention.

SUMMARY OF THE INVENTION

Figure 1:
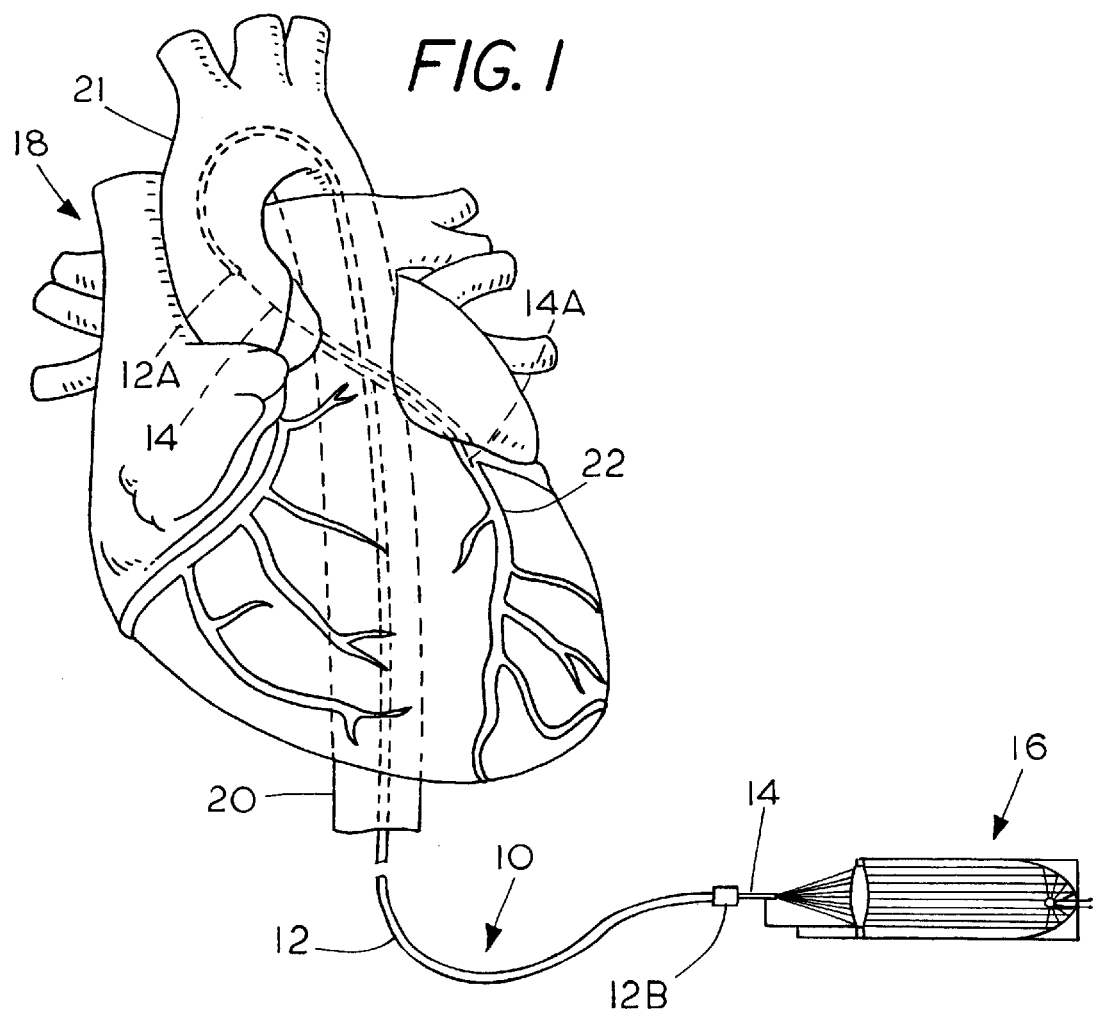
FIG. 1 is a diagrammatic elevational view showing a method and apparatus in accordance with the invention for treating coronary atherosclerosis.

Briefly, the present invention concerns a method and apparatus for eliminating atherosclerotic vascular disease by the exposure of the interior lining of the artery or other vessel to visible or ultraviolet light energy of a selected spectrum, to thereby sterilize the artery, eradicating infectious pathogens, and reversing the pathogenesis of atherosclerotic artery disease.

An apparatus is described for insertion into the body of a patient through a blood vessel for eliminating microorganisms from the interior of the blood vessel by treating atherosclerosis through the application of light energy. The light energy can be supplied through a fiber optic bundle positioned via an intra-arterial catheter that is connected to an appropriate light radiation source located outside of the body during treatment. In another form of the invention, the light energy is produced by means of a light energy source located at the distal tip of the instrument positioned centrally within the atherosclerotic plaque formation during treatment. In this case, the power source and the distal tip of the instrument can, for example, be a light emitting diode (LED) or a transparent tube containing a chemical light source or a chemiluminescent substance for producing cool light energy within the body to destroy the pathogenic microorganisms in the surrounding tissue.

DETAILED DESCRIPTION OF THE INVENTION

The therapeutic method in accordance with the present invention is suited for use in various vessels including, but not limited to, the heart, brain and peripheral vessels and can also be used with various devices, fabrication methods, arrangements, systems and methods of employment which irradiate the walls of various vessels within the body of a patient by means of radiation in sufficient amount to debilitate or kill microorganisms lining the vessel in which the invention is used without significant damage to body tissue.

In order to provide a better understanding, the present invention will be described by way of example in the treatment of coronary artery disease. It should be understood, however, that the invention is not limited to specific apparatus or methods described. During treatment, light radiation damages the microorganisms e.g. by producing apoptosis or programmed cell death in which the DNA of the microorganism is rendered unable to divide. The apoptosis that occurs in the microorganism prevents it from further replication. Consequently, the microorganisms die by mutation and, in some cases, by the disruption of metabolic processes at the cellular level. Some fraction of the microorganisms may also be killed immediately by the radiation. An important advantage of the invention lies in the fact that many organisms, such as bacteria, are exquisitely sensitive to light radiation, sensitive to a much greater degree than the surrounding human cells. The present invention provides a way in which the bacteria can be killed or debilitated without significant damage or destruction of the host cells.

Figure 2:
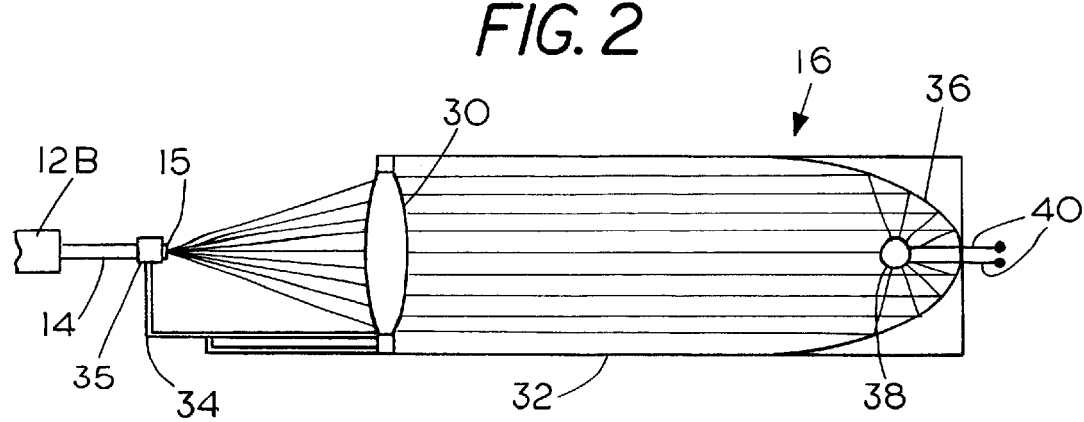
FIG. 2 is an enlarged view of an illumination device used for supplying a light energy for treating the patient.
Figure 3:
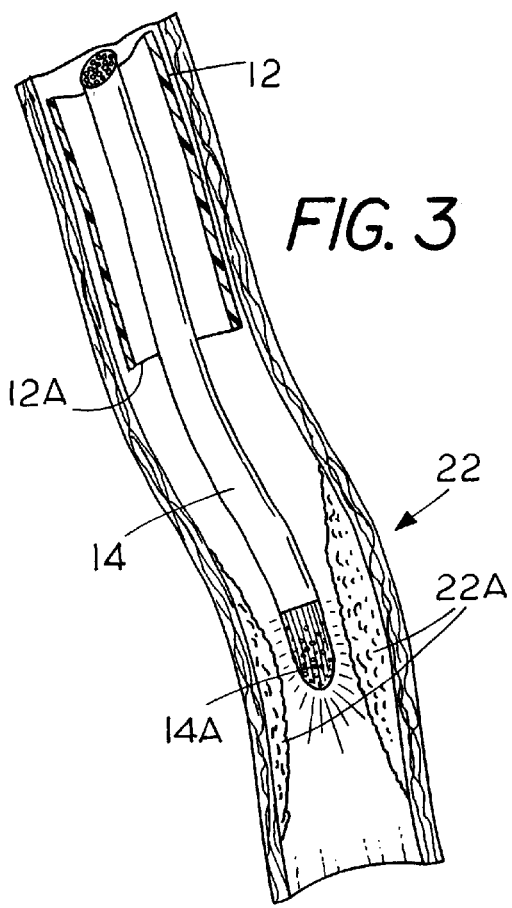
FIG. 3. is a diagrammatic longitudinal sectional view on a greatly enlarged scale showing the distal end of the fiber optic bundle of FIGS. 1 and 2 within a coronary artery.

Refer first to FIGS. 1–3 which illustrate how the present invention utilizes light energy and especially visible or ultraviolet light of a selected spectrum for killing infectious pathogens within the circulatory system so as to sterilize the interior of a blood vessel, artery or vein. Light energy is applied via an apparatus indicated generally by the numeral 10 which includes a fiber optic bundle 14 that may be, for example, about a millimeter in diameter which is delivered through a catheter 12 that is threaded in a manner similar to that now used for diagnosing and treating atherosclerosis and in conducting angioplasty or the placement of a stent. A larger diameter fiber bundle can be used for other operations. In this example, the catheter 12 is introduced through the femoral artery but it could be introduced via the arm or wrist if required. The catheter 12 is shown passing through the aorta 20 and through the aortic arch 21. The catheter 12 is positioned in the aortic arch 21 in the same manner used in angiography for diagnosing the extent of the atherosclerosis. Thus in the method used in the present invention, the catheter 12 is placed in the aortic arch or other artery or vein conventionally. The fiber optic bundle 14 is then passed through the catheter 12, exiting through the distal end of the catheter 12A and is then passed in this example into the coronary artery 22 so that the distal end 14A of the fiber optic bundle 14 is located as shown in FIG. 3 in close proximity to the occlusion at the narrow point of the artery 22 containing the atherosclerotic plaque 22A.

The fiber optic bundle can, for example, comprise spun glass bundle having substantial flexibility to allow proper positioning into an artery or vein. A typical fiber bundle 14 can contain as many as 200 separate quartz fibers. To prevent solarization of the fiber optics, the fiber bundle is hydrogen loaded and can be formed from fused quartz provided with an aluminum buffer. One suitable fiber bundle is a UVI or UVM fiber optic bundle manufactured by Polymicro Technologies of Phoenix, Ariz. By using a fiber optic bundle of this composition, minimal attenuation of the radiation occurs within the fiber optic bundle due to solarization. Solarization is an undesirable blackening of the fibers caused by energy absorption.

As shown in FIG. 3, the distal end 14A can be tapered and rounded at its extreme end to expose the ends of the fibers as illustrated enabling light to pass out of the free end of the fiber optic bundle 14 which serves as a light energy distribution head for illuminating the surrounding plaque formation 22A so as to kill or debilitate the pathogenic microorganisms present in the plaque and the vessel without ablation or other damage to the tissue of the body.

Refer now especially to FIG. 2. which illustrates the light energy or illumination supply 16 including a glass condensing lens 30 mounted upon a base 32 with a bracket at its left end in the figure supporting a collar 35 to hold the proximal end 15 of the fiber optic bundle 14 which projects somewhat from the proximal end 12B of the catheter 12. The lens 30 focuses collimated light to a point where it enters the fiber optic bundle 14. The fiber bundle is held by the collar 35 at the focal point of the light rays that pass through the lens 30. Light is provided by a light source 38 that is placed at the focal point of a three-dimensional parabolic mirror 36. Power is supplied to the lamp 38 by means of conductors 40.

A variety of different kinds of light sources can be used including a laser, a source of ultraviolet light such as a low pressure mercury lamp, a source of visible light such as an incandescent lamp, a flash lamp such as a xenon flash lamp, an arc lamp, a combination mercury-xenon lamp, an Excimer laser, a tunable dye laser or light emitting diode which will be described below. Light can also be provided by cool light sources such as chemical or chemiluminscent sources. Although the wavelength of the light use can be varied, a preferred range is a spectrum between about 200 nm and 470 nm. One preferred lamp 38 comprises either an ultraviolet lamp, such as a low pressure mercury vapor lamp, or a flash lamp formed from fused quartz, e.g. a xenon arc flash lamp, that can be made to pulse or flash periodically at selected timed intervals. One suitable flash lamp comprises a filtered short-arc xenon lamp as a radiation source for producing ultraviolet radiation. While radiation at various wavelengths can be used, one preferred range is ultraviolet light of about 200–400 nm. Good results have been obtained in debilitating pathogenic bacteria with a xenon flash lamp producing UV light between about 240–280 nm having a substantial portion thereof between about 250–270 nm, with a 258 nm peak being optimal for typical pathogenic bacteria. The flash lamp is operated by a triggered discharge of energy from an electrolytic storage capacitor contained in a suitable power supply (not shown) to produce a very short burst of high intensity light. A computerized control also contained in the power supply actuates a commercially available triggering circuit which causes the xenon gas to suddenly become a low resistance path, at which time the energy stored in the electrolytic capacitor discharges through the flash lamp or tube 38, resulting in a short duration, brilliant burst of visible light radiation that contains ultraviolet light. The computer causes the lamp to flash at selected timed intervals, e.g., every five seconds, but the interval can be changed as desired by reprogramming the computer. The radiation from the lamp is emitted from the end 14A the fiber bundle and spreads out in all directions, to thereby debilitate or kill the pathogenic microorganisms, e.g. *H. pylori* that are present in the vessel.

During use, the light energy, which can include both visible and ultraviolet light, blankets and penetrates the wall of the vessel 22 from the interior so as to kill any pathogenic microorganisms that exist in the vessel wall 22 or in the plaque 22A itself.

For various applications, visible light can be used. In one preferred form of the invention, visible blue light is employed. Blue light can be produced by an incandescent lamp or other suitable lamp with wavelengths predominantly between about 300 nm to 470 nm. An important feature of the present invention is the ability of the light radiation of the distribution head 14A to kill the microorganisms without permanently damaging the body cells or tissue or the inner lining of the artery as previously occurred when gamma or beta radiation was used to prevent restenosis of a coronary artery after angioplasty. While the invention has been described by way of example in treating a coronary artery it can be used on any part of the body that has been damaged by atherosclerosis including peripheral vascular disease, cerebral disease, etc., where microorganisms are a contributing factor to the disease condition.

Figure 4:
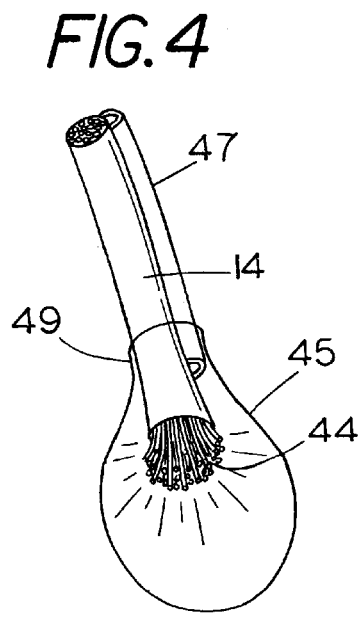
FIG. 4 is a view of a fiber optic bundle as in FIG. 3 with a modified energy distribution head.

Refer now to FIG. 4 which shows a modified form of the invention wherein the distribution head portion 44 of the fiber optic bundle 14 is enlarged somewhat so that the fibers are spread apart and to some degree those near the periphery turn outwardly so as to distribute the light energy more uniformly in all directions. In addition, the distribution head 44 is surrounded by a transparent inflatable balloon 45 into which a saline solution, air or other inflation fluid is introduced through an inflation duct 47. The balloon 45 is securely bonded at 49 to the outer surface of the fiber bundle 14 enclosing the head so that when inflated, the balloon 45 occludes blood flow temporarily to allow better penetration of the light energy from the distribution head 44 into the vessel wall and into the plaque.

Figure 5:
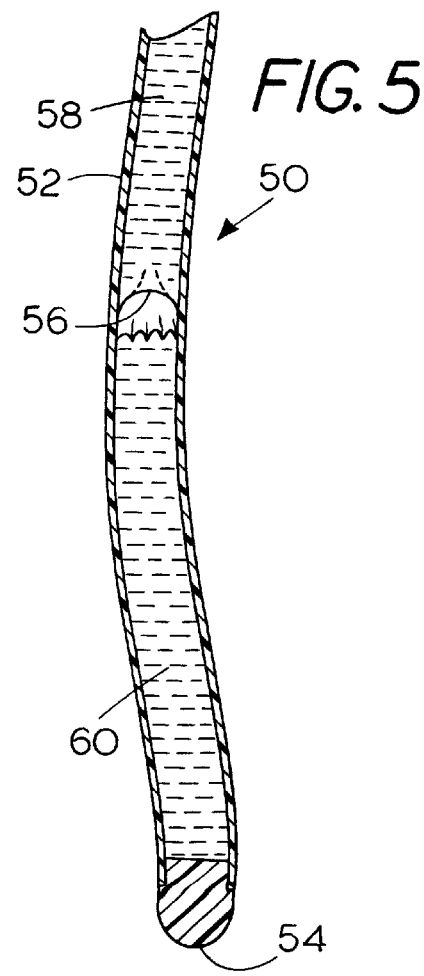
FIG. 5 is a partial longitudinal sectional view of another form of light energy distribution unit.

Refer now to FIG. 5 which shows another form of the invention. In FIG. 5 the fiber optic bundle 14 is replace by a tube 50 having generally the same dimensions as the fiber optic bundle and including a thin, flexible side wall 52 of any suitable transparent plastic composition that can be well tolerated by the body tissue. After the tube 50 has been formed, a flexible plastic film barrier 56 is securely bonded e.g., by adhesive bonding to its inner wall. The barrier 56 is of a weaker plastic film than the wall 52 of the tube 50. Once the barrier 56 is in place, the tube is filled with two chemically reactive chemiluminescence liquids 58 and 60. The distal end of the tube 50 is then sealed with a closure element 54 that can be securely bonded in place e.g., by means of an adhesive or heat. The tube 50 which serves as a light distribution head, is then stored indefinitely until it is to be used. Just before use, the tube is manipulated to apply pressure to the tube in the area of the barrier 56 which deflects the walls inwardly increasing the pressure within the tube enough to cause the barrier 56 to rupture as shown by dotted lines in FIG. 5 allowing the chemically reactive chemiluminescent liquids 58 and 60 to mix, producing a chemical reaction which causes the fluid to luminesce so as to provide a cool light radiation for killing the pathogenic microorganisms within the atherosclerotic vessel in the same manner described hereinabove. The light source within the tube 50 is allowed to remain in place within the vessel as long as required to accomplish the desired treatment. In this example, light is produced by a chemical agent or by a chemiluminescent agent. An advantage of using a chemical or chemiluminescent liquid is that the light radiation is of a cool variety which is absorbed by the microorganisms and is lethal to them but produces little if any heat which can be sensed and will not damage surrounding tissue of the patient. A variety of chemiluminescence substances can be employed such as luminal and lucigenin. Among the preferred liquids are the oxilaic ester and hydrogen peroxide with an efficient fluorescer and catalyst as disclosed in U.S. Pat. No. 3,597,362, which is incorporated herein by reference.

Other kinds of fluorescent compounds include: the conjugated polycyclic aromatic compounds examples of which are anthracene, benzanthracene, phenanthrene, naphthacene, pentacene, perylene, perylene violanthrone, and the like and their substituted forms.

Typical substituents for all of these are phenyl, lower alkyl ($C_1$-$C_6$), chloro, bromo, cyano, alkoxy ($C_1$-$C_{16}$), and other like substituents, which do not interfere with the light-generating reaction can be used.

The preferred fluorescers are 9,10-bis(phenylethynyl) anthracene, 1-methoxy-9,10-bis(phenylethynyl) anthracene, perylene, 1,5-dichloro 9,10-bis(phenylethynyl) anthracene, rubrene, monochloro and dichloro substituted 9,10-bis (phenylethynyl) anthracene, 5,12-bis(phenylethynyl) tetracene, 9,10-diphenyl anthracene, and 16,17-dihexyloxyviolanthrone.

The lifetime and intensity of the chemiluminescent light emitted can be regulated by the use of certain regulators such as: (1) by the addition of a catalyst, which changes the rate of reaction of hydroperoxide. Catalysts which accomplish that objective include those described in M. L. Bender, Chem. Revs., Vol. 60, p. 53 (1960). Catalysts can also be used which alter the rate of reaction or the rate of chemiluminescence including those accelerators of U.S. Pat. No. 3,775,366, and decelerators of U.S. Pat. Nos. 3,691,085 and 3,704,231, or (2) by the variation of hydrogen peroxide. Both the type and the concentration of hydrogenperoxide are critical for the purposes of regulation.

Of the catalysts tried, sodium salicylate and various tetraalkylammonium salicylates have been the most widely used. Lithium carboxylic acid salts, especially lithium salicylate, lithium 5-t-butyl salicylate and lithium 2-chlorobenzoate are excellent catalysts for low temperature hydrogen peroxide/oxalate ester/fluorescer chemiluminescent systems.

As outlined hereinabove, chemical light is produced by mixing reagents e.g., an oxalate ester and hydrogenperoxide together in the presence of a catalyst and a fluorescer. Typically, fluorescers are chosen that are peroxide stable to provide a long lasting glow. In most instances, a single fluorescer has been used to produce a particularly colored light. In some cases, two or more fluorescers of essentially equivalent stability in peroxide have been mixed to produce a blended color. As an example, a blue emitting fluorescer will be mixed with a red emitting fluorescer to make a pink light.

Of the numerous fluorescers described herein, relatively few emit light in peroxyoxalate chemiluminescence and are sufficiently peroxide stable (five phenylethynyl anthracenes, one violanthrone, and three perylene dicarboximides) to yield commercially viable products. While other fluorescers are known to emit light they are not peroxide stable, and have historically been rejected for commercial use. See U.S. Pat. No. 6,267,914. All publications and patents are herein incorporated by reference to the same extent as if each individual publication or patent was specifically and individually indicated to be incorporated by reference.

Refer now to FIG. 6 which illustrates another embodiment of the invention employing chemiluminescence. In FIG. 6, the fiber optic bundle 14 is replaced by a flexible shaft or cable 72 formed from solid metal or plastic such as stainless steel or polyester or polyamide plastic which is threaded into the vessel that requires treatment in the same manner described above in connection with the fiber optic bundle 14. At the distal end of the unit is a light distribution head 74 comprising a flexible capsule formed from transparent plastic typically about 1–3 mm in diameter but which is shown greatly enlarged in the figure. The capsule is attached securely to the distal end 75 of the cable 72 over a circular groove 76 into which the upper end 78 of the capsule is tightly pressed. Within the capsule is a chemiluminescent liquid 80 and a small rupturable pouch 82 that can be made from plastic film containing a different reactive chemiluminescent liquid 84. The light producing shaft and head assembly which is indicated generally at 70 is stored indefinitely in the condition shown in the figure until just before use at which time pressure is applied manually to the head 74 causing the sidewalls to be deflected inwardly rupturing the pouch 82 and allowing the liquids 80 and 84 to mix and react chemically so as to luminesce within a blood vessel while positioned as shown in FIG. 3. The capsule 74 which serves as a light distribution head is placed in the area that is narrowed by the plaque formation 22A of FIG. 3. The liquid within the capsule continues to luminesce during the time period required for treatment so that light radiation of the wavelength selected bathes the diseased tissue in light which penetrates the plaque formation and the walls of the surrounding artery or other vessel thereby debilitating or killing the microorganisms within the plaque and surrounding tissue.

Refer now to FIG. 7, which illustrates another form of a light-producing head 90 in accordance with the invention. In this case, a flexible, elongated and solid shaft or cable 92 has a hollow capsule 94 formed from a transparent plastic material fastened securely at 96 to its distal end. Within the hollow capsule 94 is an electroluminescent liquid chemical 98 of a suitable commercially available composition. Located in spaced apart positions at the ends of the capsules 94 are a pair of electrodes 100 and 102 to which electric current is supplied through conductors 104 and 106 at the upper portions of which extend through the cable 92 to an external electrical power source (not shown) that is used to provide an electric current to the electrodes 100 and 102 so as to excite the electroluminescent chemical 98 causing the liquid to luminesce while the electric current is being applied. As described hereinabove, the light produced by the capsule penetrates into the atherosclerotic plaque or tissue so as to debilitate or kill the microorganisms therein without substantial damage, ablation or destruction of the host tissue, i.e., the body tissue of the patient. The capsule is allowed to remain in the vessel being treated for as long as required to accomplish the desired destruction of the microorganisms.

Refer now to FIG. 8. which illustrates another light producing device 110 for treating atherosclerosis including a flexible plastic shaft or cable 112 similar to cable 92. Extending throughout the length of the cable 112 are electrical conductors 114, 116 which terminate at their distal ends in sockets 114A and 116A. Mounted on the distal end of the cable is a light emitting diode (LED) indicated generally by the numeral 115. Light emitting diode 115 has a pair of power supply contacts 117 and 119 which are plugged into the sockets 114A and 116A, a semiconductor chip 118 and a contact wire 120 which extends from the chip 118 to the contact 117. The contacts and chip are in this case embedded within a solid transparent plastic casing 122 such as epoxy plastic. The diameter of the casing 122 is made small enough e.g. about 1–3 mm in diameter so that it can be inserted into the vessel that requires treatment. Once inserted a current is supplied to the conductors 114 and 116 causing the LED to provide light of a selected spectral range most preferably in the range between about 300–470 nm. An important advantage of the LED 115 is its ability to provide cool light radiation that is highly effective in destroying the microorganisms present in the plaque and surrounding vessels without damaging the tissue of the patient. The LED is turned on and allowed to remain in place for a period of time required for effective treatment so as to achieve light sterilization of the atherosclerotic vascular disease. If desired, the semiconductor chip 118 can be replaced by a light emitting plastic (LEP) in which the semiconducting material is organic. Any suitable commercially available organic semiconducting material such as a PPV polymer of derivative thereof can be used. During use, the chemical composition of the PPV polymer changes its physical and electricooptical properties in producing light radiation.

If desired, in any of the embodiments of the invention described hereinabove, an optional and appropriately suitable light-sensitizing medication can be used such as any of the protoporphyrin compounds known to those skilled in the art for preferentially absorbing the light radiation so as to furnish a more effective bactericidal action. One suitable sensitizing agent is aminoleveivinic acid. Another suitable sensitizer comprises a psorlen such as demethylchlortetracycline. Other suitable known sensitizers can be employed if desired. The photosensitizer employed should be matched to the wavelength of the light provided so that the light is absorbed by the particular photosensitizer that is used. Other sensitizing agents will be apparent to those skilled in the art once the principals described herein are understood. Although helpful in some situations, photosensitizers are not an essential feature of the invention.

Many variations of the present invention within the scope of the appended claims will be apparent to those skilled in the art once the principles described herein are understood.

What is claimed is:

1. An apparatus for the use of treating atherosclerotic vascular disease within the body of a patient, said apparatus comprising,
    an instrument body having an elongated shaft that is sized and constructed for insertion into the interior of an atherosclerotic blood vessel of a patient,
    a light radiation source connected to the shaft for destroying or debilitating microorganisms within the vessel,
    said light radiation source is adapted to expose a interior wall of the vessel to light radiation with a wavelength of a selected rang to kill or debilitate pathogenic microorganisms supported on or within the plaque or endothelium lining the vessel that is being treated without damage, destruction or ablation of the vessel or the surrounding body tissue and
    the light radiation source consists of cool light producing little or no heat that can be sensed and consisting of wavelengths between about 300 nm and 470 nm such that the microorganisms are killed or debilitated without destruction of the blood vessels of the patient.

2. The apparatus of claim 1 wherein the shaft comprises a fiber optic bundle and the apparatus includes means for focusing a beam of light from the radiation source onto a proximal end of the fiber optic bundle.

3. The apparatus of claim 2 wherein a lens is provided proximate the light source to focus a collimated beam of light from the light source onto the proximal end of the fiber optic bundle passing through the shaft.

4. The apparatus of claim 1 wherein the light radiation source comprises an incandescent lamp for providing visible light energy.

5. The apparatus of claim 1 wherein the light source is a light emitting diode.

6. The apparatus of claim 5 wherein the shaft is an elongated flexible element having electrical conductors extending therealong and the light emitting diode is connected to the conductors at a distal end of th element and is adapted to be positioned by means of the shaft during use within vessel of the patient at the site of the atherosclerotic vascular disease.

7. The apparatus of claim 1 wherein the shaft is a fiber optic bundle that has a light distributing distal end and a balloon surrounds the distal end for occluding the vessel thereby enclosing the distal end such that light therefrom passes through said balloon.

8. The apparatus of claim 1 wherein the light source is a transparent container enclosing a chemiluminescent agent so as to isolate the chemiluminescent agent from the body of the patient.

9. The apparatus of claim 8 wherein the light source is a transparent plastic capsule containing a chemiluminescent agent.

10. The apparatus of claim 8 wherein the light source is a transparent tube containing a chemiluminescent agent and electrodes are electrically coupled to the light source for passing an electric current therethrough.

11. The apparatus of claim 8 wherein the light source comprises two chemically reactive agents separated by a barrier at can be removed by manipulating the light source, thereby causing the agents to react chemically for producing light energy.

12. A method of treating atherosclerotic vascular disease comprising, providing a flexible shaft that is constructed, sized and arranged to enter the vascular system including an artery or vein of a human patient or animal suffering from atherosclerotic vascular disease, providing a source of cool visible light energy consisting of a selected wavelength between about 300 nm and 470 nm, providing a said shaft with a light energy distribution head at a distal end thereof for distributing the light energy from the end of the shaft, placing the shaft into the body of the patient, positioning the distribution head within the portion of a blood vessel where the atherosclerotic disease is located, distributing light energy from the distribution head so as to kill or debilitate pathogenic microorganisms that are present in the vessel or in plaque lining the vessel said light energy reducing or eliminating or more of the symptoms of vascular inflammatory disease present in vessel or in plague lining the vessel without damage, destruction or ablation of a wall of the vessel or the surrounding body tissue.

13. The method of claim 12 including, providing the distribution head with a container that is transparent to the light energy, enclosing a chemiluminescent agent within the transparent container of the distribution head so as to isolate the chemilluminescent agent from the body of the patient and, causing the chemiluminescent agent to luminescence for producing said light energy.

14. The method of claim 13 including the step of providing at east two chemically reactive materials for forming said chemiluminescent agent, providing a removable barrier between said two chemical reactive materials and removing said barrier to enable the reactive material to mix for causing the luminescence of said chemiluminescent agent.

15. The method of claim 14 wherein the barrier is removed by manipulating the distribution head.

16. The method of claim 12 including the step of, providing a light emitting diode within the distribution head and, applying an electric current to the diode for producing said light energy.

17. The method of claim 13 including the step of applying an electrical current across said chemiluminescent agent to facilitate the production of light energy thereby.

* * * * *